United States Patent [19]
Martinez

[11] Patent Number: 5,584,880
[45] Date of Patent: Dec. 17, 1996

[54] ORBITAL IMPLANT

[76] Inventor: Miguel Martinez, 1880 W. Sunset Knoll La., Tucson, Ariz. 85704

[21] Appl. No.: 234,039

[22] Filed: Apr. 28, 1994

[51] Int. Cl.⁶ ............................................. A61F 2/14
[52] U.S. Cl. ..................... 623/4; 623/16; 433/201.1
[58] Field of Search .................. 623/4, 16, 17; 433/201.1

[56] References Cited

U.S. PATENT DOCUMENTS

| | | | |
|---|---|---|---|
| Re. 34,307 | 7/1993 | Perry | 623/11 |
| 2,667,645 | 2/1954 | Moulton . | |
| 4,702,930 | 10/1987 | Heide et al. | 623/16 |
| 4,976,731 | 12/1990 | Perry . | |
| 5,089,021 | 2/1992 | Vachet . | |
| 5,171,281 | 12/1992 | Parsons et al. | 623/17 |
| 5,192,315 | 3/1993 | Jacob-LaBarre | 623/4 |
| 5,211,661 | 5/1993 | Shinjou et al. | 623/16 |
| 5,466,259 | 11/1995 | Durette . | |

FOREIGN PATENT DOCUMENTS

| | | | |
|---|---|---|---|
| 4140326 | 6/1993 | Germany | 623/4 |

OTHER PUBLICATIONS

"The Ophtimplant: A new soft microporous ePTFE spherical implant for evisceration and enucleation," Brochure from Oculo-Plastik, Inc., Montreal, Canada, pp. 1-7, (Sep. 1990).

"Natural Movement for an Artificial Eye," Advertisement by Integrated Orbital Implants, Inc., San Diego, California, Sep. 23, 1991.

"Knitted Fabrics," Brochure from Meadox Medicals, Inc., Oakland, New Jersey, pp. 1-2, (1992).

"Velour Fabrics," Brochure from Meadox Medicals, Inc., Oakland, New Jersey, pp. 1-2, (1992).

*Primary Examiner*—Paul B. Prebilic

[57] ABSTRACT

An orbital implant for use after evisceration or enucleation of an eye includes a core and at least one porous hydroxylapatite granule mounted on the core to promote incorporation of the implant into the fibro-vascular tissue of the eye. In one embodiment, a plurality of hydroxylapatite granules form a substantially spherical layer around a polymeric core. A synthetic covering surrounds the hydroxylapatite granules for attaching the muscles of the eye to the implant. Alternatively, a polymeric spherical core is provided with at least one cavity formed on an exterior surface, and at least one porous hydroxylapatite granule is mounted in the cavity. The implants may include an integral protrusion adapted to couple with an artificial eye. Further, a tubular, synthetic fabric can be used to cover the implants by gathering the tubular fabric at open ends and welding them closed in the vicinity of recesses formed in the outer surface of the core.

22 Claims, 4 Drawing Sheets

ORBITAL IMPLANT

BACKGROUND OF THE INVENTION

1. Field of the Invention

The present invention relates generally to prosthetic systems for the eye and, more particularly, to an orbital implant for use after evisceration or enucleation of the eye.

2. Discussion of the Background Art

Under certain conditions it is necessary or desirable to remove the human eye because of disease or tissue trauma. Surgical procedures for the removal of an eye, such as evisceration and enucleation, usually include the replacement of the removed eye with a prosthetic system to restore a more normal appearance, maintain the normal structure of the eyelids and eyebrows, and to help stimulate normal growth of the orbital bones in children. The prosthetic system typically includes a sphere for use as an orbital implant and a glass or plastic shell for use as an artificial eye.

After evisceration, the orbital implant is inserted into the residual scleral sac thru a lateral incision to fill the void created by removal of the contents of the eye. In the case of enucleation, the entire eye including the scleral sac is removed, and the orbital implant is inserted directly into the orbital cavity.

Early implantations following enucleation of the eye typically involved closing the orbital cavity around the orbital implant and fitting an artificial eye to the conjunctiva. Because the artificial eye was not connected to the implant, however, realistic tracking of the artificial eye could not be achieved. In fact, even when the artificial eye was somehow connected to the orbital implant, tracking of the artificial eye to the natural eye remained inadequate since the implant merely floated within the orbital cavity. Hence, efforts have been made to attach the ocular motor muscles of the enucleated eye to the implant to produce good tracking of an artificial eye connected to the implant. U.S. Pat. No. 2,667,645 to Moulton, for example, describes the manufacture of a spherical implant from a bio-compatible, synthetic material over part of which is fixed a metal mesh corset. Clips are used to attach some of the ocular motor muscles of the enucleated eye to the metal mesh corset to improve tracking of the artificial eye. In implants employing metallic meshes and clips, however, there is a significant risk of intraorbital trauma and of the implant being rejected. U.S. Pat. No. 5,089,021 thus discloses a spherical core coated with a substantially uniform layer of a microporous, bio-compatible synthetic material such as microporous polytetrafluorethylene, or "GORE-TEX". The synthetic material is intimately mated to the spherical core by adhesive bonding or by stitching which protrudes into the core. The ocular motor muscles may then be attached to the implant with sutures.

In order to avoid the shortcomings associated with materials which are not natural to the human body, it has been proposed in U.S. Pat. No. 4,976,731 to either fill a residual scleral sac after evisceration or, in the case of an enucleation, to place within a scleral sac obtained from a tissue bank, a sphere of low-density, porous hydroxylapatite of the kind obtained from coral or by synthetic means. Hydroxylapatite has the unique biological properties of fully integrating with the surrounding eye tissue while not creating a foreign body reaction or inflammation. It promotes ingrowth by inducing the proliferation of new bone cells (osteocytes), new connective tissue (fibroblasts) and neovascularization and is thus incorporated into the scar tissue and fibro-vascular tissue that develops following surgery. After implantation and recovery, the implant can be drilled or otherwise modified to permit coupling with an artificial eye.

The hydroxylapatite material is expensive, however, and as a consequence of its porosity, tends to fill with fluids in vivo, increasing the weight of the implant. Additionally, procedures for implanting spheres of hydroxylapatite have proven to be time consuming. For example, in the case of enucleation, the hydroxylapatite sphere has typically been wrapped in donor sclera which is difficult to maintain and must be sewn together to form a scleral sac. Furthermore, openings must be formed in the scleral sac by the surgeon immediately prior to inserting the implant into the orbital cavity, in order to expose the hydroxylapatite sphere to the surrounding eye tissue. When used after evisceration, the hydroxylapatite sphere has first been wrapped in a covering to ease insertion and the covering subsequently removed from the scleral sac.

Other disadvantages of known orbital implants include the requirement for a second procedure to drill the implant in order to fit an artificial eye, difficulty in sterilizing the implant material and donor tissue, and the use of complicated and time consuming suturing techniques to cover the implant.

SUMMARY OF THE INVENTION

Accordingly, it is a primary object of the present invention to overcome the aforementioned disadvantages of the prior art and to provide orbital implants with hydroxylapatite granules mounted thereon for use after evisceration, enucleation or secondary implantation thereby promoting incorporation of the implant into the fibro-vascular structure of the eye.

It is another object of the present invention to form a spherical layer of hydroxylapatite granules around a core material to promote ingrowth of the fibro-vascular tissue anywhere on the implant.

It is a further object of the present invention to position hydroxylapatite granules at predetermined locations around a core to make effective use of the hydroxylapatite in order to reduce the cost of the prosthetic system.

The present invention has another object in that a protrusion is integrally formed as part of the orbital implant prior to implantation to couple with an artificial eye thereby obviating the need for a second surgical procedure to fit the artificial eye.

An additional object of the present invention is to cover an orbital implant with a synthetic fabric to facilitate anchoring of the eye muscles to the implant.

Advantages of the orbital implant of the present invention include effective use of hydroxylapatite material to promote ingrowth of the fibro-vascular tissue into the orbital implant at reduced expense and with less in vivo fluid retention, simplified manufacture using no bonding agents which can adversely affect the porosity of the hydroxylapatite or covering materials, and ease of use, both in insertion of the implant and fitting of the artificial eye following insertion.

The present invention is generally characterized in an orbital implant having a core and at least one porous hydroxylapatite granule mounted on the core to promote incorporation of the implant into the fibro-vascular tissue of the eye. In one embodiment, a plurality of hydroxylapatite granules form a substantially spherical layer around a polymeric core. A synthetic covering surrounds the hydroxylapatite granules for attaching the muscles of the eye to the implant. Alternatively, a polymeric spherical core is provided with at least one cavity formed on an exterior surface, and at least one porous hydroxylapatite granule mounted in the cavity. The implants may also include an integral protrusion adapted to couple with an artificial eye. Further, a tubular, synthetic fabric can be used to cover the implants by gathering the tubular fabric at open ends and welding them closed in the vicinity of recesses formed in the outer surface of the core.

Another aspect of the present invention is generally characterized in a method of making an orbital implant in which a hemispherical cavity of a mold is lined with granules of porous hydroxylapatite to form a hemispherical layer of hydroxylapatite granules, the hemispherical cavity is filled with a molten polymeric material, the molten polymeric material is cooled to form a first hemispherical part, and a second hemispherical part is formed using the same method and joined to the first hemispherical part to form an orbital implant having a polymeric core and a substantially spherical outer layer of hydroxylapatite granules. In a preferred embodiment, filling of the hemispherical cavity with a molten polymeric material includes the steps of arranging a plurality of polymeric pellets within the lined hemispherical cavity, and heating the mold above a melting point of the polymeric pellets for a first predetermined time to melt the pellets. Additionally, the step of joining the first and second hemispherical parts may include the steps of arranging a circular base of the first hemispherical part atop a circular base of the second spherical part and heating the arranged hemispherical parts above a melting point of the polymeric material for a second predetermined time.

A further aspect of the present invention is generally characterized in a method of making an orbital implant in which a bio-compatible sphere is inserted into a tube of polymeric fabric, and at least one open end of the tube is gathered against the sphere until the fabric conforms to an outer surface of the sphere. The gathered end of the tube is then melted to close the end and to fix the polymeric material around the sphere. The bio-compatible sphere may advantageously be provided with at least one recess so that after the gathering and melting steps, the melted end of the polymeric fabric can be tamped into the recess to securely affix the fabric around the sphere.

Other objects and advantages of the present invention will become apparent from the following description of the preferred embodiments taken in conjunction with the accompanying drawings wherein like parts in each of the several figures are identified by the same reference characters.

DESCRIPTION OF THE PREFERRED EMBODIMENTS

Figure 1:
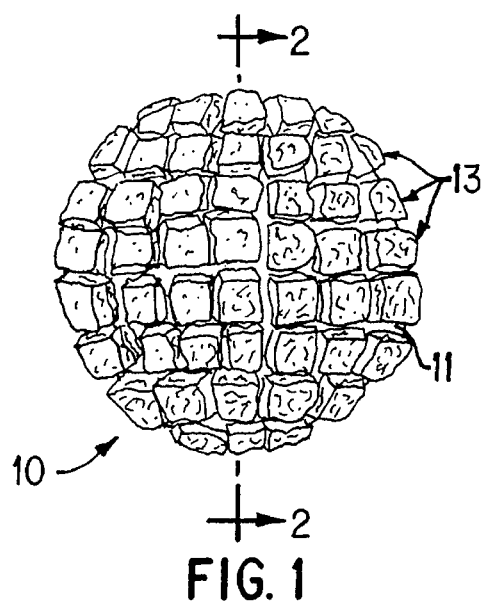
FIG. 1 is a plan view of a first embodiment of the orbital implant according to the present invention.
Figure 2:
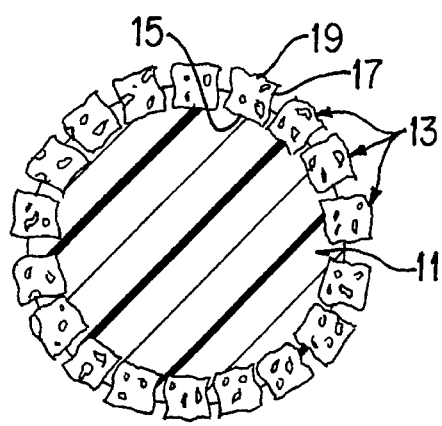
FIG. 2 is a sectional view of the orbital implant of FIG. 1 taken along line 2—2.
Figure 3:
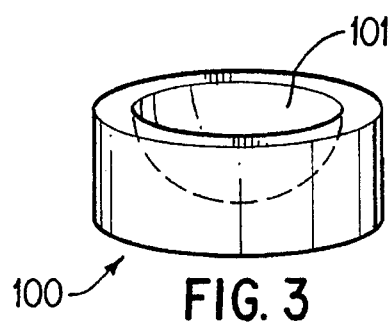
FIG. 3 is a perspective view, partly in section, of a mold for use in making orbital implants according to the present invention.

An orbital implant 10 according to the present invention is shown in FIGS. 1 and 2. The implant 10 includes a polymeric core 11 surrounded by a substantially spherical layer of porous hydroxylapatite granules 13. The granules 13 are closely spaced cubic parallelepipeds each having a bottom face 15 embedded in the polymeric core 11, four vertical side walls 17 and a top face 19. Top faces 19 of granules 13 form a discontinuous but substantially spherical outer surface having a diameter D determined by the surgeon according to the type of procedure (i.e., evisceration, enucleation or secondary implantation) and the physical characteristics of the patient (e.g., the size of the orbital cavity), but typically ranging from about 14 mm to about 22 mm.

Granules 13 are preferably brick-like granules of 99.6%–100% hydroxylapatite about 3—4 mm on each side having a porosity of about 80%±5% by volume and pore sizes of between about 200 and 600 µm, with 200–300 µm pores being particularly preferred. Granules meeting these requirements are available from Bioland Biomateriaux of Toulouse, France, and are designated Biosel SP. Three millimeter square cubes of about 75% hydroxylapatite, such as those marketed for use in filling bone defects, may also be used, and Biosel 2 offered by Bioland is exemplary of such products. Suitable hydroxylapatite particles of between 2.8 and 5.6 mm are also available from Bio-Interfaces, Inc., of San Diego, Calif.

Core 11 is a solid spheroid with an irregular outer surface extending into gaps formed between side walls 17 of adjacent granules 13 and the larger pores of the individual granules 13. The core 11 is made from a bio-compatible polymeric material, such as virgin polyethylene (e.g., REXENE, 2053, NAT, 24.00 MF, 0.921, V, distributed by Plastics General, Inc., Tempe, Ariz., or other medical grade polyethylene materials), polypropylene (e.g., Amoco No. 4018, available from Orange Products, Inc., Allentown, Pa.), polyester, nylon, polytetrafluoroethylene (TEFLON) or silicone rubber.

Figure 4:
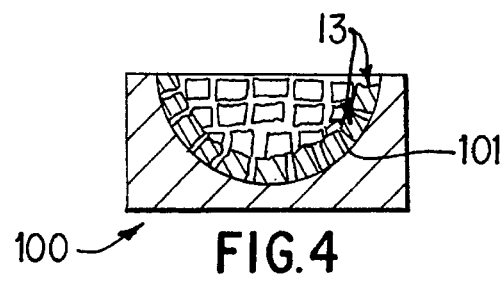
FIG. 4 is a side view of the mold, partly in section, showing granules of hydroxylapatite lining an interior surface of the mold.

A simple method of producing the orbital implant 10 is illustrated in FIGS. 3–7 using a cylindrical aluminum mold 100 having a hemispherical concavity 101 concentrically defined on a top face of the cylinder. The diameter of the hemispherical concavity 101 corresponds approximately to the desired diameter of the finished orbital implant 10 (i.e., between about 14 and about 22 mm in diameter). Using forceps to grasp individual hydroxylapatite granules 13, the hemispherical concavity 101 is lined with the hydroxylapatite granules 13 as shown in FIG. 4. This creates a layer of hydroxylapatite granules 13, the packing density of which is governed by the geometry of the individual hydroxylapatite granules 13. For example, when cubic granules are used as shown, wedge shaped spaces are defined between the side walls 17 of individual granules 13. However, if wedge shaped granules are used to line the hemispherical concavity 101, an essentially continuous hydroxylapatite layer can be formed.

Figure 5:
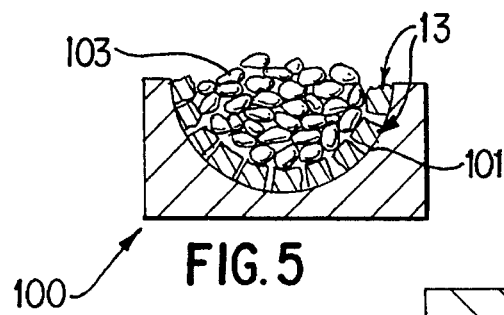
FIG. 5 is a side view of a mold, partly in section, showing placement of polymeric pellets in the cavity of the mold.
Figure 6:
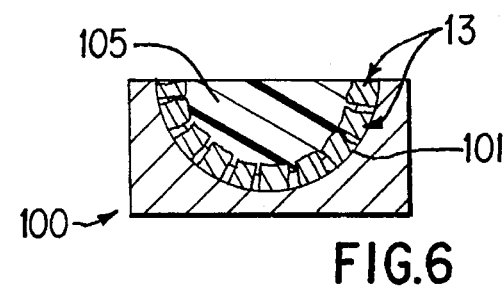
FIG. 6 is a side view of the mold, partly in section, showing the hardened configuration of the polymeric material.
Figure 7:
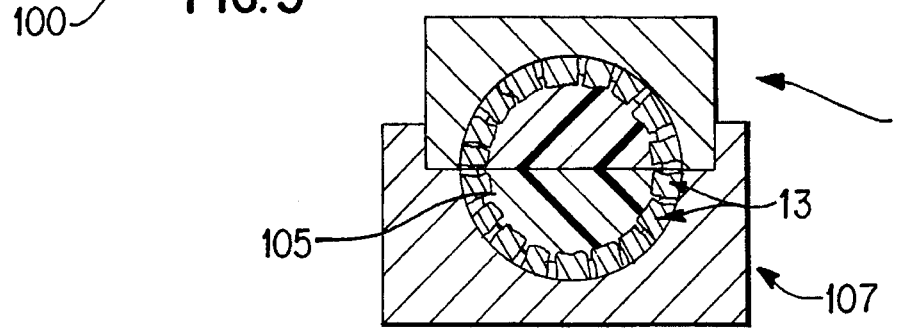
FIG. 7 is a side view, partly in section, of an orbital implant made up of two halves being joined according to the method of the present invention.

As shown in FIG. 5, spheroidal pellets 103 of a polymeric material are stacked on top of the hydroxylapatite granules 13 lining concavity 101 in sufficient amount to fill the interior space defined by the hydroxylapatite layer when the pellets 103 are in a molten state. The polymeric pellets 103 are then heated until melted to conform to the shape of the interior space defined by the hydroxylapatite layer and allowed to cool forming a solid core 105 embedding the hydroxylapatite granules 13 as shown in FIG. 6. The resulting hemispherical part is one half of an orbital implant 10. A second hemispherical part is produced in the same manner in another cylindrical mold 107 adapted to mate with the first mold 100 to define a spherical cavity therebetween. With the two hemispherical parts held between mating molds 100 and 107 as shown in FIG. 7, a spherical implant 10 is formed by heating the molds 100 and 107 to melt their polymeric cores 105 together.

EXAMPLE

If polymeric pellets 103 are polyethylene, the hemispherical concavity 101 of mold 100 is lined with hydroxylapatite granules 13 and loaded with pellets 103 in the manner previously described. The mold 100 is then heated to a temperature of about 350° F. for approximately fifteen minutes or until the polyethylene pellets 103 freely flow. The molten polyethylene fills the space between the hydroxylapatite layer and even migrates between individual granules 13. The mold 100 is removed from the heat and allowed to cool to room temperature. The finished, hemispherical part, is half of an orbital implant. A second half is produced using the method previously described, and the two halves joined by placing the circular base of one half on top of the corresponding circular base of the other half, and reheating the two hemispherical parts for about five minutes at 350° F.

In use, the implant 10 is first sterilized using any conventional sterilization techniques, including the use of an autoclave, ethylene oxide gas, or gamma irradiation. If the contents of the patient's eye have been removed through an incision in the sclera (i.e., evisceration), the implant 10 is wrapped in plastic and inserted through the incision into the remaining scleral sac. The plastic wrap is then removed and the scleral sac sewn closed. If the entire eye has been removed including the scleral sac (i.e., enucleation), the implant 10 is sewn within a scleral sac obtained from human donor tissue, inserted into the orbital cavity and the muscles of the eye sutured to the scleral sac near openings cut into the sac by the surgeon to promote ingrowth of the tissue into the hydroxylapatite granules 13. After implantation and recovery, the implant is coupled with an artificial eye in any conventional manner.

Figure 8:
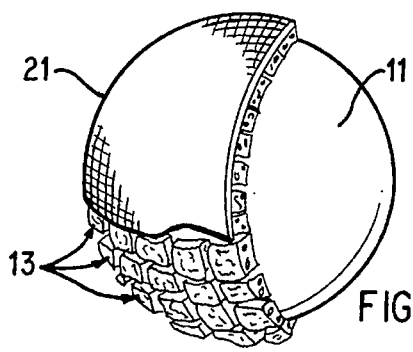
FIG. 8 is a plan view, partly in section, of an orbital implant with an integral bio-compatible covering.
Figure 9:
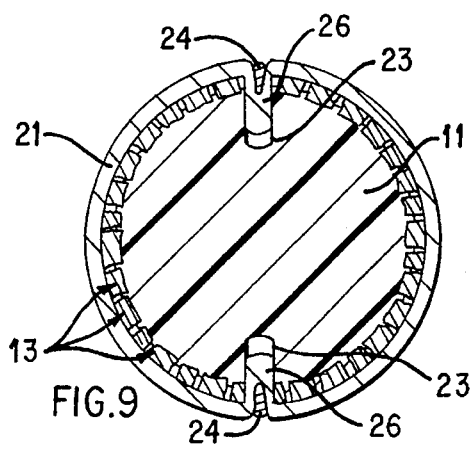
FIG. 9 is a sectional view of the orbital implant of FIG. 8.

A modification of the orbital implant 10 of the present invention is shown in FIGS. 8 and 9 wherein a synthetic covering 21 surrounds the hydroxylapatite granules 13 thereby obviating the need to use plastic wrap or human donor sclera in the implantation procedure. Polymeric core 11 and hydroxylapatite granules 13 are essentially the same as previously described, with the exception that two blind holes 23 are formed along a polar axis on opposite sides of the core 11. Covering 21 forms a layer of substantially uniform thickness around hydroxylapatite granules 13 and is gathered into blind holes 23 to fix the covering 21 to the core 11. The covering 21 is preferably a synthetic fabric of the type which promotes fibro-vascular ingrowth, made of a polymeric material such as polyester, polypropylene or polytetrafluoroethylene (TEFLON), and in the form of a mesh, knitted cloth, single or double velour fabric or a felt. Examples of suitable commercially available fabrics include MEADOX® LARS® mesh, MEADOX® TRELEX NATURAL® knitted polypropylene mesh, MEADOX® Weavenit® warp-knit fabric, MEADOX® Cooley Knitted Fabric, MEADOX® Stretch Fabric, MEADOX® Double Velour tubing, MEADOX® Cooley Double Velour, MEADOX® Single and Double Velour, MEADOX® Cooley Low Porosity, MEADOX® Woven Minicrimp™ fabric, MEADOX® Knitted Minicrimp™ fabric or MEADOX® Felts, all of which are distributed by Meadox Medicals, Inc., of Oakland, N.J.

Figure 10A:
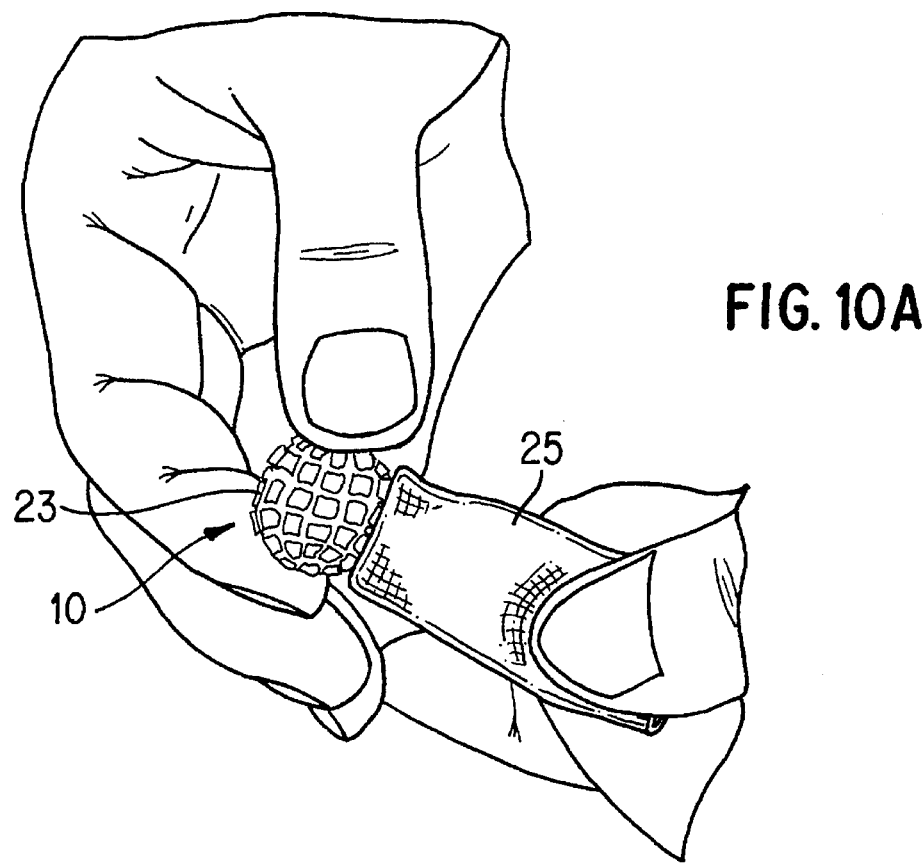
FIGS. 10A–10E illustrate a method of covering an orbital implant according to the present invention.
Figure 11:
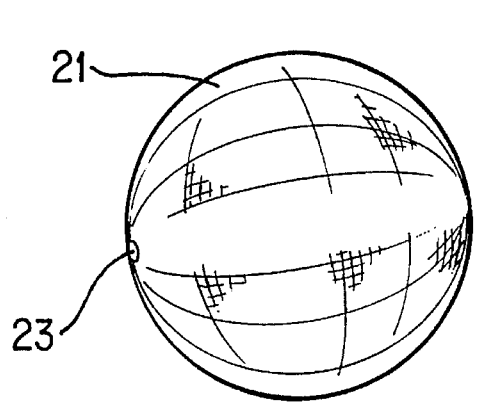
FIG. 11 is an illustration of a covered implant fabricated according to the method shown in FIGS. 10A–10E.
Figure 10B:
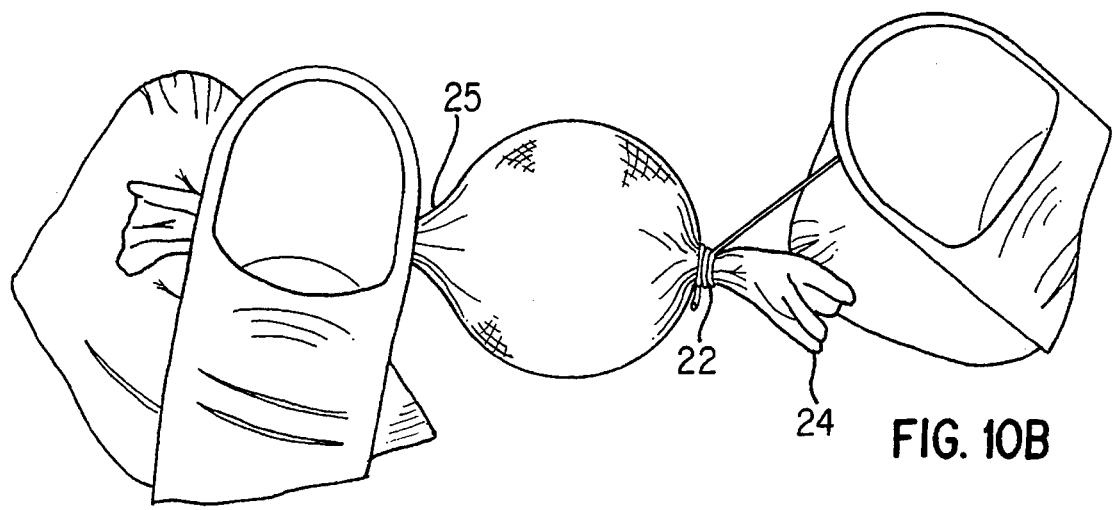
Figure 10C:
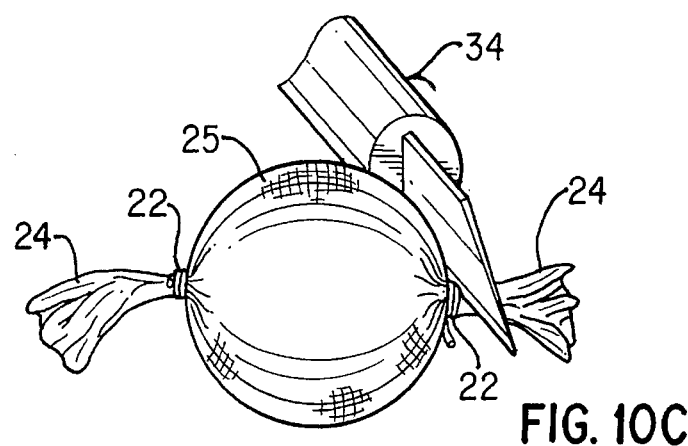
Figure 10D:
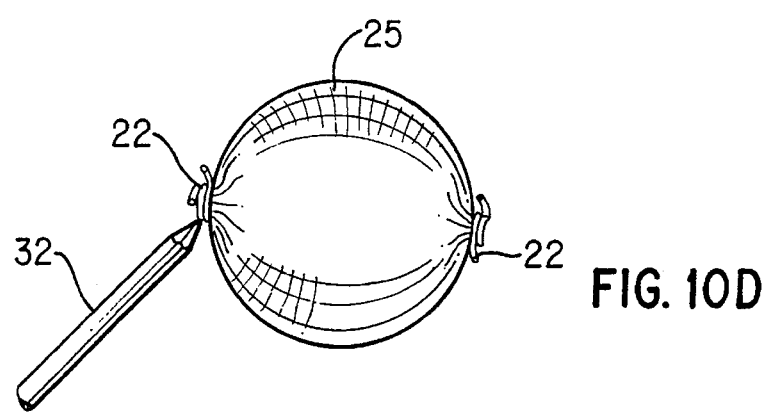
Figure 10E:
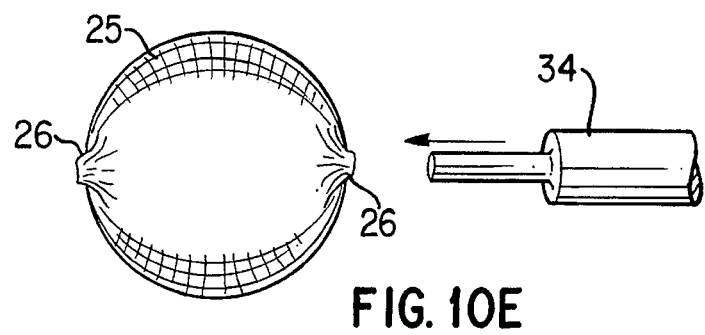

It is preferred that covering 21 be supplied initially as a tubular fabric sleeve 25 (e.g., MEADOX® Double Velour 32 mm tubing) and installed as shown in FIGS. 10A–10E. More particularly, the implant 10 is covered by holding the tubular fabric sleeve 25 with the seam on the inside and one end of the sleeve 25 clamped between the thumb and forefinger as shown in FIG. 10A. The orbital implant 10 is then inserted into the other, open end of the sleeve 25 with blind holes 23 in core 11 aligned with a longitudinal axis of the tubular sleeve 25. Both ends of the tubular sleeve 25 are gathered inward, or bunched together, in front of blind holes 23 to stretch the fabric around the implant 10, and a copper wire 22 is then wrapped around the gathered ends of the tubular sleeve 25 as shown in FIG. 10B to form 3 or 4 coils to hold the fabric tightly against the implant 10. With the ends of tubular sleeve 25 wrapped with coils of copper wire 22, excess fabric 24 is cut away from the ends (for example, with a knife blade 34) and the copper wire 22 heated with a soldering iron 32 (or some other heating device), as shown in FIG. 10D, to weld the plug of fabric material held within the coils of copper wire 22. The copper wire 22 is then removed and the rod-like plugs 26 of welded fabric tucked into corresponding blind holes 23 in the implant 10, using a punch 34 for example, as shown in FIG. 10E. Any remaining space above the welded plug 26 is filled using small pieces of fabric, such as the excess fabric 24 previously removed, and tamping the fabric down into the hole 23. A substantially smooth spherical covering 21 as shown in FIG. 11 is thus formed without the use of bonding agents that can adversely affect the porosity of either or both of the cover material and any hydroxylapatite granules used.

The manner in which the covering 21 is attached to the orbital implant 10 also eliminates the need for complicated suturing techniques which require a penetrable core material or holes to be formed in the core, and facilitates incorporation of the implant 10 within the orbital cavity by allowing the eye muscles to be sutured and attached directly to the covering 21 adjacent the top faces 19 of hydroxylapatite granules 13. Attachment of the eye muscles to the covering 21 proximate hydroxylapatite granules 13 promotes the incorporation of granules 13, and thus the implant 10, into the fibro-vascular structure of the orbital cavity. Hence, the covering 21 of the present invention dispenses with the need to use human donor sclera tissue, which can never guarantee full sterilization of the sclera, and which is difficult to obtain and preserve in glycerine or alcohol. Additionally, the smooth exterior surface of covering 21 dispenses with the need to use plastic wrap when inserting the orbital implant into the residual scleral sac after evisceration of the eye.

Figure 12:
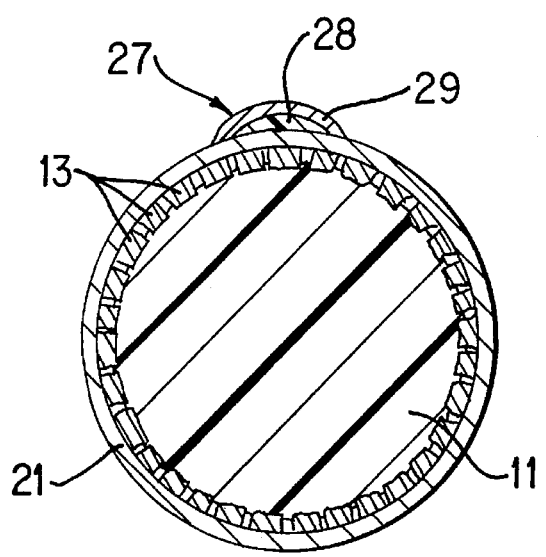
FIG. 12 is a sectional view of an orbital implant having an integral protrusion.

A further modification of the orbital implant 10 is shown in FIG. 12 and differs primarily in the provision of a blister-like protrusion 27 on an outer surface of covering 21 to couple with an artificial eye. The protrusion 27 includes a hemispheroidal insert 28 and a covering 29 which extends over the hemispheroidal insert 28 and is attached along peripheral edges thereof to the covering 21. The insert 28 is formed of a biocompatible polymeric material, such as any of the core materials listed herein and has a diameter of about 3 to about 4 mm. Covering 29 is made from the same material as covering 21 and is thus easily welded in place.

In the case of enucleation, the orbital implant of FIG. 12 is inserted into the orbital cavity with protrusion 27 facing in an anterior direction. The eye muscles are then sutured directly to the covering 21 in the vicinity of protrusion 27 to maintain the orientation of the protrusion 27 and to promote fibro-vascular incorporation of the implant as previously described. In time, vascular and fibroblastic invasion of the material of covering 21 and the hydroxylapatite granules 13 will allow an artificial eye to be fitted in the usual way by molding the prosthesis to fit the conjunctiva. A recess formed in a posterior surface of the artificial eye receives the protrusion 27 to transmit movement of the orbital implant to the artificial eye.

Figure 13:
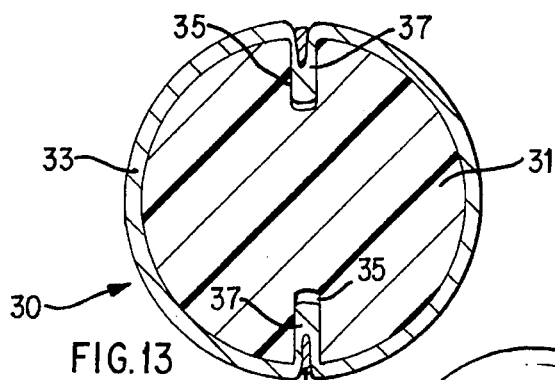
FIG. 13 is a sectional view of an orbital implant having a spherical core and a biocompatible fabric covering attached according to the method of the present invention.

Another modification of the orbital implant of the present invention is shown in FIG. 13 wherein the orbital implant 30 is a solid sphere 31 surrounded by a synthetic fabric covering 33. The sphere 31 is preferably a polymeric material such as polyethylene, polypropylene (e.g., Amoco No. 4018, available from Orange Products, Inc., Allentown, Pa.), polymethylmethacrylate (PMMA) (Engineering Laboratories, Inc., Pompton Lakes, N.J.), polyester, polytetrafluoroethylene (TEFLON), nylon or silicone rubber, and is provided with blind holes 35 formed along a polar axis on opposite sides of the sphere 31. The covering 33 is the same as covering 21 and is fixed to sphere 31 in the manner previously described with welded ends 37 tucked into blind holes 35 and filler material 39 tamped in above the welded ends 37. This configuration allows the orbital implant 30 to be manufactured without hydroxylapatite, since the bio-compatible covering 33 can achieve the desired incorporation of the orbital implant 30 to the fibro-vascular structure of the orbital cavity.

Figure 14:
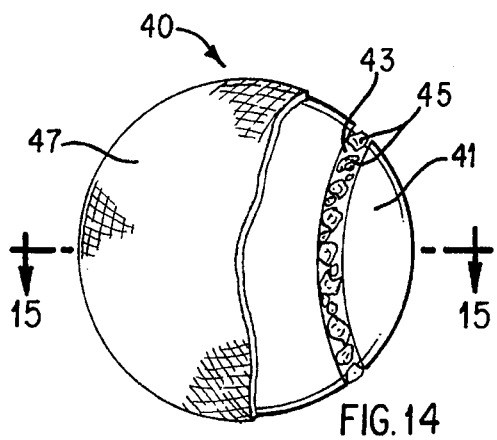
FIG. 14 is a plan view, partly in section, of an orbital implant having an annular recess in which granules of hydroxylapatite are mounted.
Figure 15:
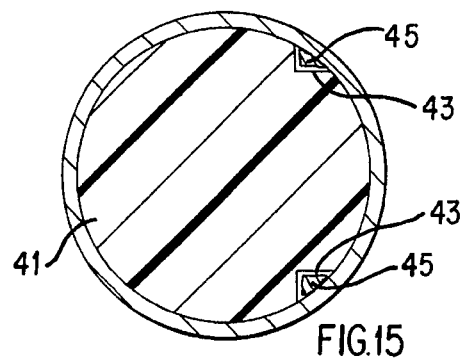
FIG. 15 is a sectional view of the orbital implant of FIG. 14 taken along line 15—15.

The orbital implant 40 illustrated in FIGS. 14 and 15 includes a sphere 41 similar to sphere 31 in orbital implant 30, with the exception that an annular recess 43 is defined on an anterior face of the sphere 41, and a plurality of hydroxylapatite granules 45 are carried within the annular recess 43 in a ring-like configuration. The depth of annular recess 43 and size of the hydroxylapatite granules 45 are chosen so as to preserve the overall sphericity of the implant 40, with about 1–2 mm for each being preferred. Additionally, a bio-compatible covering 47 similar to covering 21 surrounds sphere 41 in a conformal manner as described previously in connection with covering 21 and functions to retain hydroxylapatite granules 45. The annular configuration of the hydroxylapatite granules 45 on the anterior face of sphere 41 helps ensure that the orbital implant 40 will be incorporated into the fibro-vascular tissue of the eye when the eye muscles are sewn to covering 47 in the vicinity of the annular recess 43 and the hydroxylapatite granules 45 disposed therein.

Figure 16:
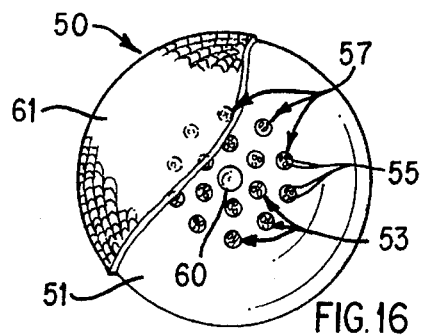
FIG. 16 is a frontal view of an orbital implant having a plurality of hydroxylapatite filled cavities and a protrusion defined by the exposed tip of an embedded peg.
Figure 17:
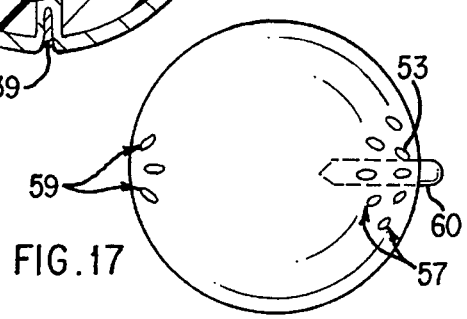
FIG. 17 is a side view of the orbital implant of FIG. 16.
Figure 18:
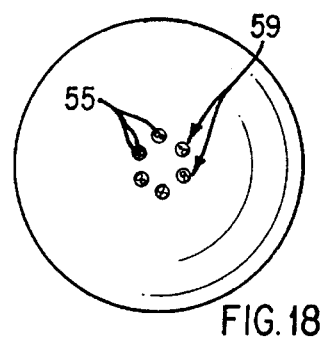
FIG. 18 is a rear view of the orbital implant of FIG. 16.

In yet another modification, shown in FIGS. 16–18, groups of annularly spaced cavities 53, 57 and 59 are defined on anterior and posterior faces of a sphere 51 to support hydroxylapatite granules or particles 55 in ring-like formations. Sphere 51 and a bio-compatible covering 61 are essentially the same as those previously described in connection with orbital implants 30 and 40, and may be fabricated using the same materials and techniques. A first plurality of cavities 57 are arranged in a ring-like configuration on an anterior face of sphere 51 concentric with a polar axis thereof to hold a plurality of hydroxylapatite granules 55. A second plurality of cavities 59 are arranged on the posterior face of the sphere 51 in a ring-like configuration axially aligned with the first plurality of cavities 57 and also hold hydroxylapatite granules 55 to promote fibro-vascular ingrowth on the posterior face of the orbital implant 50. A third plurality of cavities 53 are provided concentrically within the first plurality of cavities 57, in a ring-like formation, to promote ingrowth near the polar axis of the orbital implant 50. The positioning and size of the ring-like groups of cavities 53 and 57 is selected to correspond approximately to the locations on the anterior face of the implant where the eye muscles are normally anchored, with concentric 6 and 12 mm diameter rings made up of 1.5 and 3 mm cavities, respectively, being preferred. Granules 55 can be any size suitable for mounting within the cavities but, like granules 45, are preferably about 1–2 mm in size.

A peg 60 with a hemispherical tip is secured to sphere 51 along the polar axis forming an integral protrusion between rings 53 and 57 on the anterior face of the sphere 51 to couple with a recess formed in a posterior face of an artificial eye. The peg 60 can be made of any of the aforementioned core materials, such as PMMA, polypropylene, polyester, polytetrafluoroethylene (TEFLON), nylon or silicone rubber, and is preferably formed integrally with or made part of the core 51 prior to insertion of the implant 50 into the orbital cavity. Fixation of peg 60 to any of the orbital implants previously described, prior to insertion, obviates the need for a separate surgical procedure to drill the implant for placement of such a peg. Further, in orbital implant 50, the selective placement of the smaller group of cavities 53 immediately around peg 60 helps promote tissue ingrowth and thus secure adhesion of the patient's conjunctival tissue around the peg 60.

From the above, it will be appreciated that orbital implants according to the present invention provide a bio-compatible replacement for the eye while also facilitating the implantation procedure, reducing costs and promoting ingrowth. By "ingrowth" is meant the colonization of portions of the implant by proliferation of osteocytes, fibroblasts and neovascularization. The orbital implants are useful to replace the contents of the eye, or the eye itself, following evisceration, enucleation or secondary implantation procedures, and when provided with an integral protrusion prior to implantation, can be directly coupled to an artificial eye without surgery to improve tracking of the eye.

The orbital implant of the present invention can have various diameters depending on the type of procedure and the physical characteristics of the patient, but will typically range in diameter from about 14 mm to about 22 mm. When an integral protrusion is provided, it should extend a suitable distance, e.g., 3–5 mm, from the surface of the implant to couple with an artificial eye, and if a covered insert is used to form the protrusion, the insert can be made from single or multiple pieces of any biocompatible material, including metals, plastics, hydroxylapatite or any of the aforementioned fabrics. In those orbital implants using hydroxylapatite granules to promote ingrowth, these granules are preferably pure hydroxylapatite in synthetic form, but may also be natural hydroxylapatite from coral, or any other spongy crystalline phosphate material which promotes ingrowth and can be supported on a core material. "Granules," as used herein, refers to micro-porous or macro-porous crystalline structures of any geometry or size suitable for mounting on a core material. The particular geometry of granule chosen will affect the packing structure and hence the size of any voids between granules mounted on a core and the overall continuity of any layer formed with granules. An advantage of having spaces between granules is to provide more surface area for tissue ingrowth. Although the granules have been described as being embedded in a core or held in place with a covering material, they can be mounted using any fixation method suitable for holding the granules securely against the core material without affecting the porosity thereof. Because of the porous nature of the hydroxylapatite material, the process of embedding hydroxylapatite granules in a matrix such as the core offers the advantage of greater stability and a more secure fixation. Another advantage of embedding granules in a core is that the implant can be manufactured using irregularly sized granules which have not been machined, thus greatly reducing cost. Although a single layer of hydroxylapatite granules has been described, plural layers may also be provided to increase the depth of tissue ingrowth possible.

It will also be appreciated that when granules are used to form a spherical outer layer, the core is not necessarily spherical in shape since it is the granules which form the outer surface of the implant and the core material may migrate between individual granules. Moreover, although certain polymeric materials have been described as being suitable for use as core materials, other biocompatible core materials, such as metals and cancellous bone from animals or humans, can be used, keeping in mind that the type of material chosen will affect the method used to secure the granules to core, the weight of the implant, the ease of sterilization and the overall cost of the prosthetic device. Depending on the material chosen and the manufacturing method used, it may also be advantageous to provide a core which is solid, hollow, perforated or which contains a plurality of internal cavities. Further, where an integral covering is fixed within oppositely disposed holes or recesses by welding, these holes may be formed from individual cylindrical cavities as shown, a single through-hole drilled along a polar axis of the implant or by any other type of depression or concavity. As used herein, "welding" refers to any process of uniting gathered material into a mass.

Inasmuch as the present invention is subject to many modifications, variations and changes in detail, it is intended that all subject matter discussed above or shown in the accompanying drawings be interpreted as illustrative only and not be taken in a limiting sense.

What is claimed is:

1. An orbital implant for use after evisceration or enucleation of an eye comprising a core and a plurality of porous hydroxylapatite granules mounted on said core in spaced relation to promote tissue ingrowth therebetween, said hydroxylapatite granules and core cooperating to define an outer surface configured to fit within an orbital cavity.

2. An orbital implant as recited in claim 1 wherein said plurality of hydroxylapatite granules are of parallelepiped configuration.

3. An orbital implant as recited in claim 2 wherein said plurality of hydroxylapatite granules form a substantially spherical shell around said core.

4. An orbital implant as recited in claim 3 wherein said hydroxylapatite granules are substantially cubic.

5. An orbital implant as recited in claim 1 wherein said core is a bio-compatible polymeric material.

6. An orbital implant as recited in claim 5 wherein each of said hydroxylapatite granules is embedded in said polymeric core.

7. An orbital implant as recited in claim 6 wherein said bio-compatible polymeric material is chosen from the group consisting of polyethylene, polypropylene, polyester, nylon, polytetrafluoroethylene and silicone rubber.

8. An orbital implant comprising
   a core;
   at least one porous hydroxylapatite granule mounted on said core; and
   a synthetic, porous covering surrounding said core and said at least one hydroxylapatite granule to provide a surface for anchoring eye tissue to said orbital implant.

9. An orbital implant as recited in claim 8 wherein said porous covering is a polymeric fabric.

10. An orbital implant for use after evisceration or enucleation of an eye comprising
    a core;
    at least one porous hydroxylapatite granule mounted on said core;
    a synthetic, porous covering surrounding said core and said at least one hydroxylapatite granule to provide a surface for anchoring eye tissue to said orbital implant, wherein said porous covering is a polymeric fabric; and
    wherein a pair of openings are formed on opposite sides of said core and ends of said porous covering are gathered within said openings after welding.

11. An orbital implant as recited in claim 10 wherein said porous covering is made of a bio-compatible polymeric material chosen from the group consisting of polyester, polypropylene and polytetrafluoroethylene.

12. An orbital implant as recited in claim 8, said orbital implant further comprising a protrusion secured to said porous covering and configured to couple with an artificial eye.

13. An orbital implant for use after evisceration or enucleation of an eye comprising
    a core;
    at least one porous hydroxylapatite granule mounted on said core;
    a synthetic, porous covering surrounding said core and said at least one hydroxylapatite granule to provide a surface for anchoring eye tissue to said orbital implant;
    a protrusion secured to said porous covering and configured to couple with an artificial eye; and
    wherein said protrusion is a substantially hemispherical insert covered by a patch of porous, biocompatible polymeric fabric.

14. An orbital implant as recited in claim 1 wherein said core is substantially spherical.

15. An orbital implant comprising a spherical core and at least one porous hydroxylapatite granule mounted on said core, said hydroxylapatite granule and core cooperating to define an outer surface configured to fit within an orbital cavity, wherein at least one cavity is formed in said spherical core and said at least one hydroxylapatite granule is mounted in said cavity.

16. An orbital implant for use after evisceration or enucleation of an eye comprising a substantially spherical core having at least one cavity formed therein, wherein said at least one cavity is an annular recess defined in an anterior face of said sphere; and a plurality of hydroxylapatite granules mounted in said annular recess.

17. An orbital implant as recited in claim 15 wherein a first plurality of cavities are formed on an anterior face of said sphere and further comprising a plurality of hydroxylapatite granules mounted within said cavities.

18. An orbital implant as recited in claim 17 wherein a second plurality of cavities are formed on a posterior face of said sphere and said first and second plurality of cavities are arranged in first and second rings, respectively.

19. An orbital implant as recited in claim 18 wherein a third plurality of cavities is formed on an anterior face of said sphere and arranged in a third ring disposed within said first ring of cavities.

20. An orbital implant as recited in claim 14 and further comprising a protrusion which extends radially from said sphere to couple with an artificial eye.

21. An orbital implant for use after evisceration or enucleation of an eye comprising a spherical core with a pair of recesses formed on opposite sides of said sphere core, and a synthetic, porous covering completely surrounding said spherical core, said covering having ends gathered into said recesses.

22. An orbital implant as recited in claim 21 and further comprising a protrusion which extends radially from said spherical core to couple with an artificial eye.

* * * * *